(12) United States Patent
Mukaidani et al.

(10) Patent No.: US 8,278,499 B2
(45) Date of Patent: Oct. 2, 2012

(54) NONALCOHOLIC STEATOHEPATITIS MODEL RODENT AND FATTY LIVER MODEL RODENT

(75) Inventors: Chise Mukaidani, Higashihiroshima (JP); Katsutoshi Yoshizato, Higashihiroshima (JP); Miho Kataoka, Kumamoto (JP)

(73) Assignees: Hiroshima Industrial Promotion Organization, Hiroshima (JP); Phoenixbio Co., Ltd., Hiroshima (JP); Hiroshima University, Hiroshima (JP)

( * ) Notice: Subject to any disclaimer, the term of this patent is extended or adjusted under 35 U.S.C. 154(b) by 0 days.

(21) Appl. No.: 12/308,758

(22) PCT Filed: Jun. 13, 2007

(86) PCT No.: PCT/JP2007/061943
§ 371 (c)(1),
(2), (4) Date: Feb. 11, 2009

(87) PCT Pub. No.: WO2008/001614
PCT Pub. Date: Jan. 3, 2008

(65) Prior Publication Data
US 2009/0313710 A1    Dec. 17, 2009

(30) Foreign Application Priority Data

Jun. 29, 2006    (JP) ................................. 2006-179275

(51) Int. Cl.
*A01K 67/00* (2006.01)
*A01K 67/027* (2006.01)
*G01N 33/00* (2006.01)

(52) U.S. Cl. .................. 800/9; 800/14; 800/18; 800/25; 800/3

(58) Field of Classification Search ........................ None
See application file for complete search history.

(56) References Cited

U.S. PATENT DOCUMENTS
2005/0119463 A1    6/2005    Mukaidani et al.

FOREIGN PATENT DOCUMENTS
JP    2002-045087    2/2002
JP    2007-037542    2/2007

OTHER PUBLICATIONS

Tateno et al. American J. Pathol., 2004, vol. 165, pp. 901-912.*
Overturf et al. American J. Pathol., 1997, vol. 151, pp. 1273-1280.*
Yoshizato, Katsutoshi, "Application Prospect of Human Hepatocyte Chimeric Mice to Drug Development", *Workshop of the Japanese Society for the Study of Xenobiotics*, vol. 17:111-115. (Japanese language version accompanied by English translation.).
Tateno, Chise et al., "Human Hepatocyte Chimeric Mice", *The Pharmaceutical Monthly*, 2004, vol. 46(10):1877-1881. (Japanese language version accompanied by English translation.).
Kataoka, Miho et al., "A Human NASH Mouse Model: A Chimeric Mouse Produced by Transplanting Human Hepatocytes Isolated From Livers of UPA/SCID Mice That Had Been Near Completely Replaced With Human Hepatocytes", Hepatology, 2006, vol. 44(4) suppl. 1, p. 661A. (English language abstract.).
An Affidavit to the effect that Chise Mukaidani, Katsutoshi Yoshizato and Miho Kataoka have completed the invention published in the proceedings of the 13th Annual Meeting of the Japanese Society for the Research of Hepatic Cells with another researcher as an experimental collaborator along with Verified English translation thereof, 2005.
An Affidavit to the effect that the researcher is a mere experimental collaborator for the three inventors along with Verified English translation thereof, 2005.
An Affidavit to the effect that Chise Tateno is one and the same person with Chise Mukaidani, one of the inventors along with Verified English translation thereof, 2005.
A Certificate to the effect that the proceedings of the 13th Annual Meeting of the Japanese Society for the Research of Hepatic Cells was published on Jun. 15, 2006 along with Verified English translation thereof.

* cited by examiner

*Primary Examiner* — Deborah Crouch
(74) *Attorney, Agent, or Firm* — Wenderoth, Lind & Ponack, L.L.P.

(57) ABSTRACT

Disclosed is a nonhuman animal showing the symptoms of human nonalcoholic steatohepatitis which is obtained by transplanting human hepatocytes into an immunodeficient hepatopathic nonhuman animal to produce a chimeric nonhuman animal and then transplanting human hepatocytes that are propagated in the body of the chimeric nonhuman animal into an immunodeficient hepatopathic nonhuman animal of the same species as the immunodeficient hepatopathic nonhuman animal described above, as well as a nonhuman animal showing the symptoms of human fatty liver which is obtained by transplanting human hepatocytes into an immunodeficient hepatopathic nonhuman animal to produce a chimeric nonhuman animal.

14 Claims, 10 Drawing Sheets

Fig. 3
primary chimeric mice (Day 86 after transplantation)
H&E staining
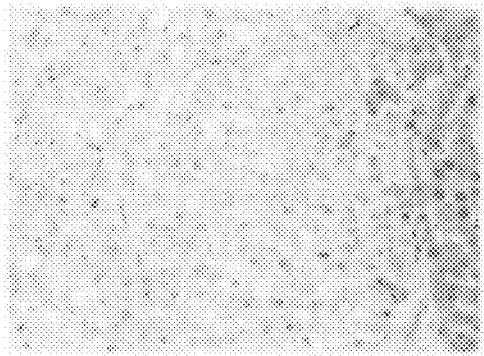
Sirius Red staining
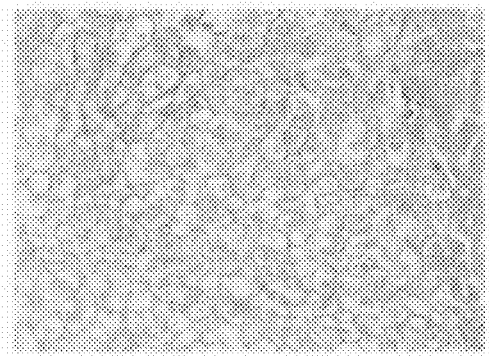
serially transplanted chimeric mice (Day 84 after transplantation)
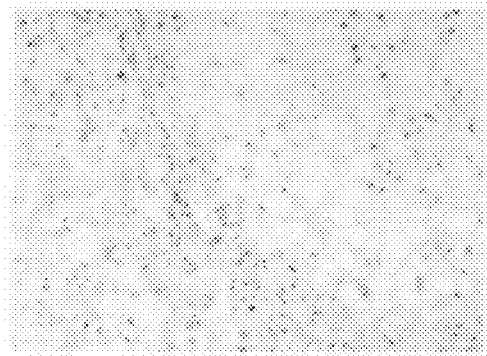
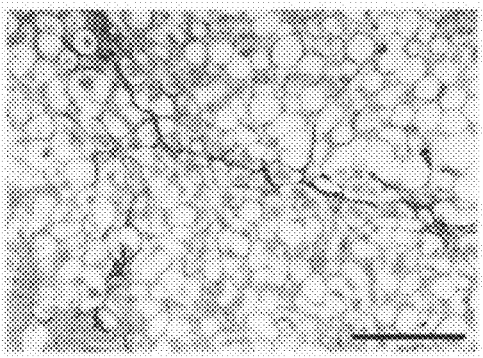
100 μm Fig. 5
serially transplanted chimeric mice
(Day 89 after transplantation)
H&E staining
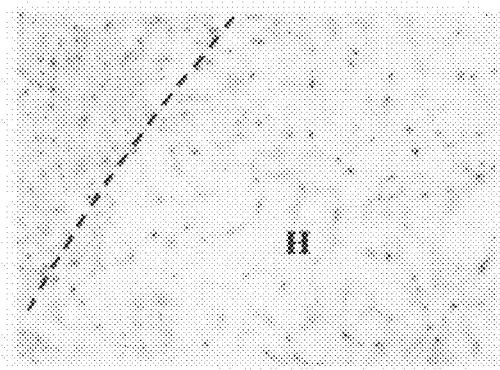
Oil Red O staining
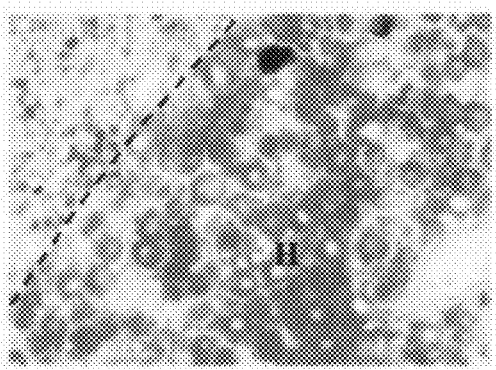
Cytokeratin 8/18
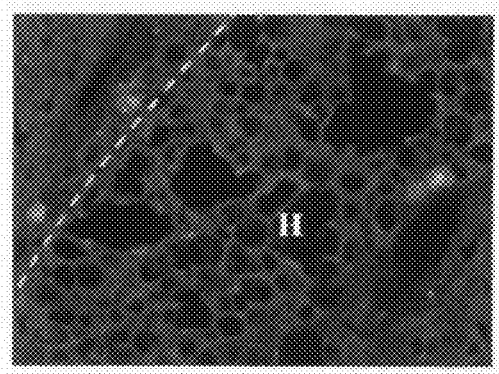
Hoechst staining
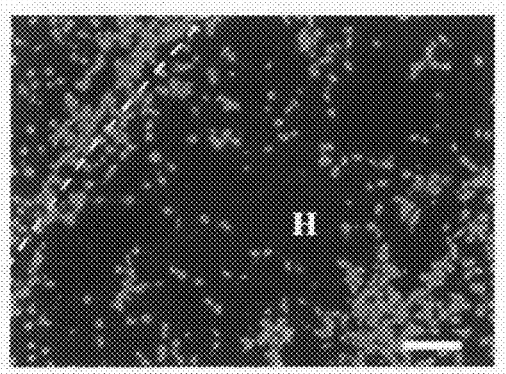
H: region of human hepatocytes    50 μm Fig. 6
serially transplanted chimeric mice
(Day 124 after transplantation)
H&E staining
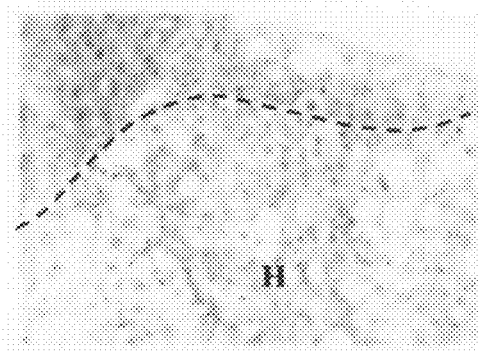
Oil Red O staining
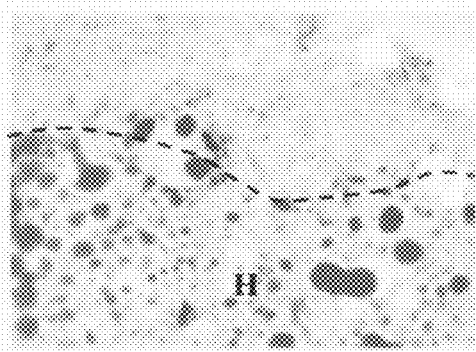
Cytokeratin 8/18
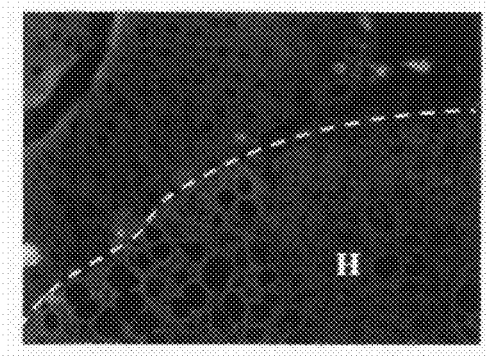
Hoechst staining
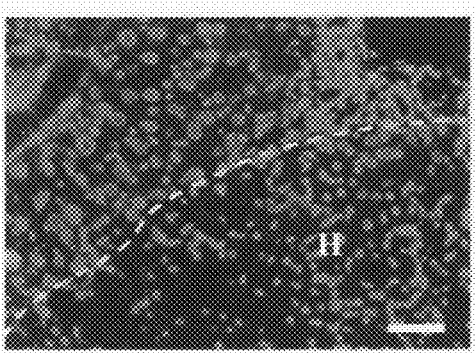
H: region of human hepatocytes
50 μm primary chimeric mice (Day 82 after transplantation)

CYP2E1               4-HNE serially transplanted chimeric mice
(Day 61 after transplantation)
CYP2E1               4-HNE (Day 84 after transplantation)
CYP2E1               4-HNE 50 μm Fig. 8
serially transplanted chimeric mice (Day 84 after transplantation)
iron staining
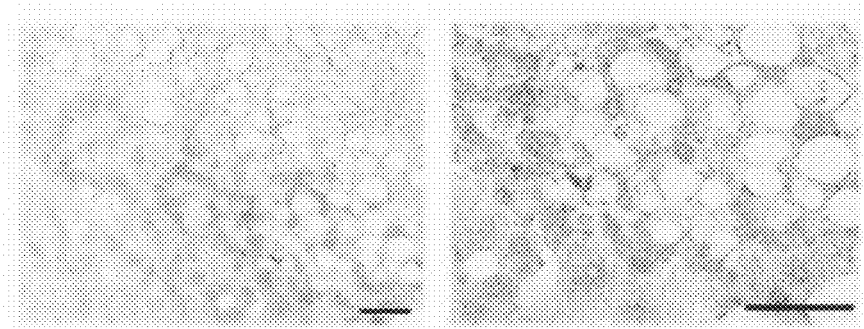
TUNEL staining  50 μm                    50 μm
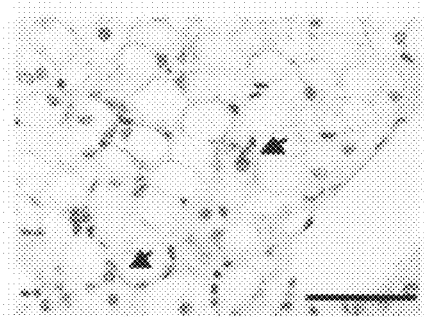
50 μm Fig. 9
primary chimeric mice
A. steatosis grade
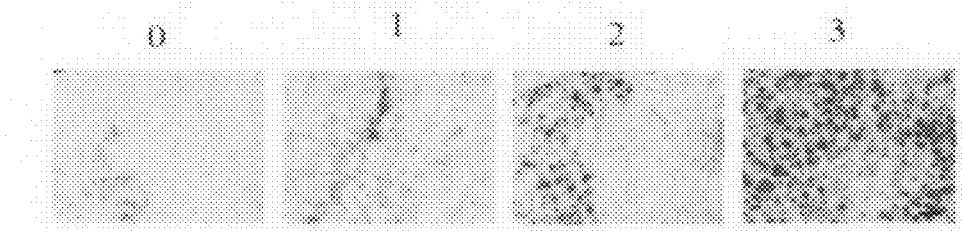
B. the relationship between steatosis grade and days after transplantation
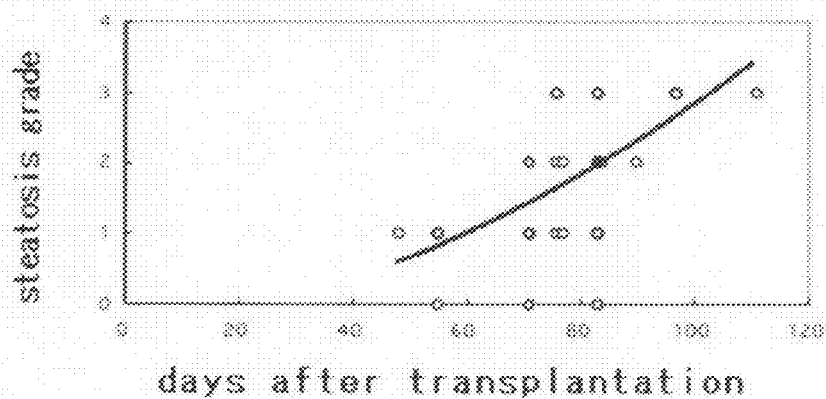

NONALCOHOLIC STEATOHEPATITIS MODEL RODENT AND FATTY LIVER MODEL RODENT

This application is a U.S. national stage of International Application No. PCT/JP2007/061943 filed Jun. 13, 2007.

TECHNICAL FIELD

The present invention relates to a nonhuman animal showing the symptoms of human nonalcoholic steatohepatitis, a human nonalcoholic steatohepatitis model animal comprising the above animal, a method of using the above animal as a human nonalcoholic steatohepatitis model animal, a method for screening a therapeutic agent for human nonalcoholic steatohepatitis by using the above animal, and a method for producing the above animal.

The present invention also relates to a nonhuman animal showing the symptoms of human fatty liver, a human fatty liver model animal comprising the above animal, a method of using the above animal as a human fatty liver model animal, a method for screening a therapeutic agent for human fatty liver by using the above animal, and a method of producing the above animal.

BACKGROUND ART

Fatty liver is a pathological condition characterized by the accumulation of lipids, mainly neutral fat, within hepatocytes, and by hepatocyte steatosis seen in ⅓ or more of hepatic lobules. Among causes of fatty liver, those of importance are probably overconsumption of nutrition, obesity, overconsumption of alcohol, diabetes mellitus, total parenteral nutrition, some drugs, malnutrition, pregnancy, etc. Once the causes are eliminated, the pathological condition can be ameliorated and prognosis is good, but in some cases, fatty lever may be accompanied by inflammation and fibrosis, thus evolving to hepatic cirrhosis.

Nonalcoholic steatohepatitis (NASH) is a disease concept related to hepatic disorder observed in those taking no alcohol, and is a disease considered attributable to such as obesity, diabetes mellitus, hypertriglyceridemia, excessive nutrient uptake due to long-term parenteral nutrition, endocrine disorder, hypo-β-lipoproteinemia, and starvation/re-supplementation syndrome. NASH attracts attention since the number of patients with NASH has been increasing in recent years. NASH is a disease considered to be encountered relatively often even in a general practice, and many of the hepatitis that are not diagnosed as alcoholic liver disease, viral hepatitis or drug-induced hepatic injury are presumably categorized in this disease. Because there is histological similarity between alcoholic steatohepatitis and NASH, it is suggested that both of them have an analogous mechanism in pathogenesis, and the study of its details is still progressing at present.

In study of the pathogenic mechanism and prophylaxis/therapy of NASH, model animals showing the symptoms of NASH are necessary. Conventionally, ob/ob mice showing obesity, fatty liver and hyperinsulinemia attributable to deficiency of leptin gene are used as model animals of fatty liver, and rats fed choline/methionine-deficient diet are used as model animals of NASH, but these model animals do not fully reproduce human NASH because their livers are those of nonhuman animal origin.

Here, JP-A 2002-45087 discloses that a uPA transgenic mouse (uPA-Tg mouse), a genetically hepatopathic mouse in which a urokinase plasminogen activator (uPA) gene ligated to an enhancer/promoter for albumin produced in the liver has been introduced into all cells, is crossed with a SCID mouse, which is an immunodeficient mouse, thereby producing a uPA/SCID mouse, i.e., an immunodeficient hepatopathic mouse. Then, human hepatocytes are transplanted into this mouse, whereby a human hepatocyte chimeric mouse in which a part of the mouse liver has been replaced by human hepatocytes can be obtained.

Further, WO 03/080821 A1 discloses that human hepatocytes are transplanted into, and simultaneously a complement inhibitor is administered to, the above uPA/SCID mouse, whereby the replacement index of human hepatocytes in the liver of the mouse can be improved.

DISCLOSURE OF THE INVENTION

Problems to be Solved by the Invention

The object of the present invention is to provide a nonhuman animal having the liver replaced with human hepatocytes to show the symptoms of human NASH, a method for producing the above animal, a method of using the above animal as a human NASH model animal, a human NASH model animal having the liver replaced with human hepatocytes, and a method for screening a therapeutic agent for human NASH by using the above nonhuman animal.

Further, the object of the present invention is to provide a nonhuman animal having the liver replaced with human hepatocytes to show the symptoms of human fatty liver, a method for producing the above animal, a method for using the above animal as a human fatty liver model animal, a human fatty liver model animal having the liver replaced with human hepatocytes, and a method for screening a therapeutic agent for human fatty liver by using the above nonhuman animal.

Means for Solving the Problems

The inventors made extensive studies to solve the problem described above, and obtained the following findings.
(i) Human hepatocytes were transplanted into a uPA/SCID mouse, which is an immunodeficient hepatopathic mouse, to produce a primary chimeric mouse, and human hepatocytes were separated from the liver of this primary chimeric mouse by a collagenase perfusion method and then transplanted into a new uPA/SCID mouse to produce a chimeric mouse. In this chimeric mouse, macrovesicular fat deposition in human hepatocytes and swelling of human hepatocytes were observed, and inflammatory cells including mainly neutrophils were accumulated around the human hepatocytes. Fibrosis image was also observed. Because these symptoms are characteristic of NASH, this mouse is considered usable as an NASH model.
(ii) In the primary chimeric mouse described above, large lipid droplets were observed in the liver, and steatosis developed such that it could be recognized in most of the hepatocytes. Because these symptoms closely resemble those of human fatty liver, this mouse is considered usable as a fatty liver model.

The present invention was completed based on these findings, and provides the following nonhuman animal and the like.
(1) A nonhuman animal showing a symptom of human nonalcoholic steatohepatitis, the nonhuman animal being obtained by a method comprising:
a first step of transplanting human hepatocytes into an immunodeficient hepatopathic nonhuman animal to produce a chimeric nonhuman animal; and a second step of transplanting human hepatocytes that are propagated in the body of the chimeric nonhuman animal into an immunodeficient hepatopathic nonhuman animal of the same species as the immunodeficient hepatopathic nonhuman animal described above, the second step being conducted once or a plurality of times.

(2) The nonhuman animal according to the above (1), which is a mammal.

(3) The nonhuman animal according to the above (2), wherein the mammal is a rodent.

(4) The nonhuman animal according to the above (1), which is obtained by the method in which the second step is conducted once.

(5) A model animal of human nonalcoholic steatohepatitis, which is obtained by a method comprising:
a first step of transplanting human hepatocytes into an immunodeficient hepatopathic nonhuman animal to produce a chimeric nonhuman animal; and
a second step of transplanting human hepatocytes that are propagated in the body of the chimeric nonhuman animal into an immunodeficient hepatopathic nonhuman animal of the same species as the immunodeficient hepatopathic nonhuman animal described above, the second step being conducted once or a plurality of times.

(6) The model animal according to the above (5), wherein the nonhuman animal is a mammal.

(7) The model animal according to the above (6), wherein the mammal is a rodent.

(8) The model animal according to the above (5), which is obtained by the method in which the second step is conducted once.

(9) A method of using a nonhuman animal as a model animal of human nonalcoholic steatohepatitis, the nonhuman animal being obtained by a method comprising:
a first step of transplanting human hepatocytes into an immunodeficient hepatopathic nonhuman animal to produce a chimeric nonhuman animal; and
a second step of transplanting human hepatocytes that are propagated in the body of the chimeric nonhuman animal into an immunodeficient hepatopathic nonhuman animal of the same species as the immunodeficient hepatopathic nonhuman animal described above, the second step being conducted once or a plurality of times.

(10) The method according to the above (9), wherein the nonhuman animal is a mammal.

(11) The method according to the above (10), wherein the mammal is a rodent.

(12) The method according to the above (9), wherein the nonhuman animal is obtained by the method in which the second step is conducted once.

(13) A method for screening a therapeutic agent for human nonalcoholic hepatitis, which comprises
a step of administering a test substance to a nonhuman animal; and
a step of comparing the degree of a nonalcoholic steatohepatitis symptom before and after administration, the nonhuman animal being obtained by a method comprising:
a first step of transplanting human hepatocytes into an immunodeficient hepatopathic nonhuman animal to produce a chimeric nonhuman animal; and
a second step of transplanting human hepatocytes that are propagated in the body of the chimeric nonhuman animal into an immunodeficient hepatopathic nonhuman animal of the same species as the immunodeficient hepatopathic nonhuman animal described above, the second step being conducted once or a plurality of times.

(14) The method according to the above (13), wherein the nonhuman animal is a mammal.

(15) The method according to the above (14), wherein the mammal is a rodent.

(16) The method according to the above (13), wherein the nonhuman animal is obtained by the method in which the second step is conducted once.

(17) A method for producing a nonhuman animal showing a symptom of human nonalcoholic steatohepatitis, which comprises
a first step of transplanting human hepatocytes into an immunodeficient hepatopathic nonhuman animal to produce a chimeric nonhuman animal; and
a second step of transplanting human hepatocytes that are propagated in the body of the chimeric nonhuman animal into an immunodeficient hepatopathic nonhuman animal of the same species as the immunodeficient hepatopathic nonhuman animal described above, the second step being conducted once or a plurality of times.

(18) The method according to the above (17), wherein the nonhuman animal is a mammal.

(19) The method according to the above (18), wherein the mammal is a rodent.

(20) The method according to the above (17), wherein the second step is conducted once.

(21) A nonhuman animal showing a symptom of human fatty liver, the nonhuman animal being obtained by a method for producing a chimeric nonhuman animal by transplanting human hepatocytes into an immunodeficient hepatopathic nonhuman animal.

(22) The nonhuman animal according to the above (21), which is a mammal.

(23) The nonhuman animal according to the above (22), wherein the mammal is a rodent.

(24) A model animal of human fatty liver, which comprises a chimeric nonhuman animal obtained by transplanting human hepatocytes into an immunodeficient hepatopathic nonhuman animal.

(25) The model animal according to the above (24), wherein the nonhuman animal is a mammal.

(26) The model animal according to the above (25), wherein the mammal is a rodent.

(27) A method of using, as a model animal of human fatty liver, a chimeric nonhuman animal obtained by transplanting human hepatocytes into an immunodeficient hepatopathic nonhuman animal.

(28) The method according to the above (27), wherein the nonhuman animal is a mammal.

(29) The method according to the above (28), wherein the mammal is a rodent.

(30) A method for screening a therapeutic agent for human fatty liver, which comprises
a step of administering a test substance to a chimeric nonhuman animal obtained by transplanting human hepatocytes into an immunodeficient hepatopathic nonhuman animal; and
a step of comparing the degree of a fatty liver symptom before and after administration.

(31) A method for producing a nonhuman animal showing a symptom of human fatty liver, which comprises transplanting human hepatocytes into an immunodeficient hepatopathic nonhuman animal to produce a chimeric nonhuman animal showing a symptom of human fatty liver.

(32) The method according to the above (31), wherein the nonhuman animal is a mammal.

(33) The method according to the above (32), wherein the mammal is a rodent.

Effect of the Invention

It was found in the present invention that when human hepatocytes were transplanted into an immunodeficient hepatopathic nonhuman animal to produce a chimeric animal, and human hepatocytes were separated from the chimeric animal and transplanted into a new immunodeficient hepatopathic nonhuman animal of the same species, thereby producing a serially transplanted chimeric animal, the liver of this chimeric animal has a histological image that is characteristic of NASH. The degree of NASH symptoms in the hepatic tissue of this serially transplanted chimeric animal is remarkably significant as compared with that of the primary chimeric animal.

The serially transplanted chimeric animal accurately reproduces human NASH because the whole or a part of the liver has been replaced by human hepatocytes.

It follows that as a model animal accurately showing the pathology of human NASH, this serially transplanted chimeric animal can be preferably used in study of the pathogenic mechanism of NASH and in screening an agent for prophylaxis/therapy of NASH.

Further, it was found in the present invention that the liver of the primary chimeric animal has a histological image that is characteristic of fatty liver. As a model animal accurately showing the pathology of human fatty liver, this primary chimeric animal can be preferably used in study of the pathogenic mechanism of fatty liver and in screening an agent for prophylaxis/therapy of fatty liver.

BRIEF DESCRIPTION OF DRAWINGS

FIG. 3 shows the HE-stained images and the Sirius Red-stained images of the primary chimeric mouse liver (Day 86 after transplantation) and the serially transplanted chimeric mouse liver (Day 84 after transplantation).

FIG. 5 shows the results of HE staining, Oil Red O staining, immunostaining for cytokeratin 8/18 and Hoechst staining of serial sections from the liver of the serially transplanted chimeric mouse (Day 89 after transplantation).

FIG. 6 shows the results of HE staining, Oil Red O staining, immunostaining for cytokeratin 8/18 and Hoechst staining of serial sections from the liver of the serially transplanted chimeric mouse (Day 124 after transplantation).

FIG. 8 shows the results of iron staining and TUNEL staining in the serially transplanted chimeric mouse liver (Day 84 after transplantation).

FIG. 9 Panel A is the Oil Red O stained-image of the primary chimeric mouse liver. Panel B is a graph showing the relationship between steatosis grade and days after transplantation in the primary chimeric mice.

BEST MODE FOR CARRYING OUT THE INVENTION

Figure 1:
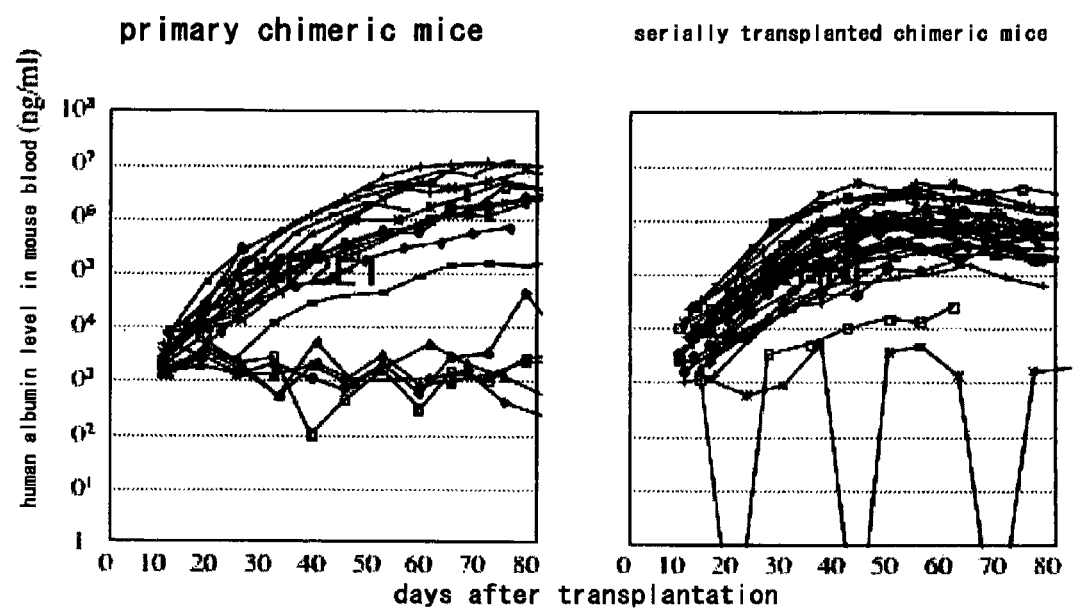
FIG. 1 shows the time course of blood human albumin levels in the primary chimeric mice and in the serially transplanted chimeric mice.

Hereinafter, the present invention will be described in detail. First, a method for producing a nonhuman animal showing the symptoms of human NASH will be described, and then the nonhuman animal and its use will be described. Furthermore, a method for producing a nonhuman animal showing the symptoms of human fatty liver will be described, and then the nonhuman animal and its use will be described.
(I) Method for Producing a Nonhuman Animal Showing the Symptoms of NASH The method for producing a nonhuman animal showing the symptoms of human NASH according to the present invention comprises a first step of producing a chimeric nonhuman animal by transplanting human hepatocytes into an immunodeficient hepatopathic nonhuman animal and a second step of producing a serially transplanted chimeric nonhuman animal showing the symptoms of NASH by transplanting human hepatocytes that are propagated in the body of the chimeric nonhuman animal into an immunodeficient hepatopathic nonhuman animal of the same species as the immunodeficient hepatopathic nonhuman animal described above. The method of the present invention also comprises a method in which the second step is conducted twice or more.

Human NASH is a generic term of liver diseases marked by fat accumulation other than human alcoholic liver disease, and refers to a disease showing at least following symptoms in the liver: lipid droplet deposition, inflammatory cell infiltration, and fibrosis. Usually, NASH does not include viral liver diseases, but includes liver diseases attributable to drug-induced hepatic injury.

In the present invention, the nonhuman animal (hereinafter referred to sometimes as "animal") is preferably a mammal, more preferably a rodent. Examples of the rodent include such as mice, rats, guinea pigs, squirrels and hamsters, among which mice and rats used widely as experimental animals are easily used.

Immunodeficient Hepatopathic Nonhuman Animal

The immunodeficient hepatopathic nonhuman animal is a nonhuman animal whose innate hepatocytes have been impaired and whose immunity has been also impaired not to exhibit rejection against cells derived from animals of different species. Because the innate cells of the animal have been impaired, the animal after transplanted with human hepatocytes will have its liver functions maintained by the transplanted human hepatocytes and accurately reflecting intraindividual functions of the human hepatocytes. In addition, the transplanted human hepatocytes will easily grow.

The immunodeficient hepatopathic animal can be produced by subjecting the same individual to hepatopathy induction treatment and also to immunodeficiency induction treatment. Examples of the hepatopathy induction treatment include administration of hepatopathy inducers such as carbon tetrachloride, yellow phosphorus, D-galactosamine, 2-acetylaminofluorene and pyrrolodine alkaloid, as well as surgical removal of a part of the liver. Examples of the immunodeficiency induction treatment include such as administration of immunosuppressive agents and thymectomy.

The immunodeficient hepatopathic animal can also be produced by subjecting a genetically immunodeficient animal to hepatopathy induction treatment. Examples of the genetically immunodeficient animal include an animal with severe combined immunodeficiency (SCID) showing T-cell failure, an animal that has lost T-cell functions by genetic deficiency of thymus, and an animal whose RAG2 gene has been knocked out by a known gene targeting method (Science, 244:1288-1292, 1989). The specific examples include SCID mice, NUDE mice and RAG2 knockout mice.

Alternatively, the immunodeficient hepatopathic animal can be produced by subjecting a genetically hepatopathic animal to immunodeficiency induction treatment. Examples of the genetically hepatopathic animal include transgenic animals produced by a known transgenic method (Proc. Natl. Acad. Sci. USA 77; 7380-7384, 1980) using a hepatopathy-inducing protein gene ligated under the control of an enhancer and/or a promoter for a protein expressed specifically in hepatocytes. Such animals have hepatopathy because the hepatopathy-inducing protein is expressed specifically in the liver. Examples of the protein expressed specifically in the liver include serum albumin, cholinesterase and a Hageman factor. Examples of the hepatopathy-inducing protein include a urokinase plasminogen activator (uPA), a tissue plasminogen activator (tPA), etc. Further, an animal having genetic hepatopathy, for example, can also be obtained by knockout of a gene that bears liver functions, such as a fumarylacetoacetate hydrolase gene.

Furthermore, the immunodeficient hepatopathic animal can also be produced by crossing a genetically immunodeficient animal with a genetically hepatopathic animal of the same species as the genetically immunodeficient animal.

The genetically immunodeficient hepatopathic animal to be used is preferably an animal whose hepatopathy-inducing gene is homozygous. In such a homozygous animal, normal hepatocytes hardly proliferate, and thus innate hepatocytes of the animal do not prevent proliferation of human hepatocytes. However, such a homozygous animal can be obtained with probability only 1/4, when hemizygotes are crossed with each other.

On the other hand, a genetically immunodeficient hepatopathic animal whose hepatopathy-inducing gene is hemizygous ("hemizygous immunodeficient hepatopathic animal") can be obtained with probability 1/2 when hemizygotes are crossed with each other or when a hemizygote is crossed with a genetically immunodeficient animal, and thus it can be produced at low cost. However, in the hemizygous immunodeficient hepatopathic animal, one of diploid chromosomes is normal, so that deletion of a hepatopathy-inducing gene allows normal hepatocytes to proliferate while forming colonies, thus increasing the proportion of normal hepatocytes in the liver after birth. It is therefore preferable that a substance that specifically inhibits hepatocyte proliferation is administered to the animal before transplantation of human hepatocytes into the hemizygous immunodeficient hepatopathic animal, to prevent normal hepatocytes from proliferating to form colonies. Examples of the substance that inhibits hepatocyte proliferation include a kind of pyrrolodine alkaloid such as retrorsine, lasiocarpine, seneciphylline, monocrotaline or trichodesmine.

Human Hepatocytes

Human hepatocytes to be used for transplantation may be those separated from normal human hepatic tissues by a method known in the art, such as collagenase perfusion. Further, the separated hepatocytes may also be cryopreserved and then used after thawing.

The age of a human from which hepatocytes are separated is not particularly limited. For example, human hepatocytes from children under 14 years of age can be used to attain a high replacement index of human hepatocytes.

Proliferative hepatocytes having an active proliferative ability in vivo are preferably used. In the present invention, "proliferative hepatocytes" refer to human hepatocytes that form a colony as a population of a single cell strain under culture condition (in vitro) and grow so as to make the colony larger. Further, this growth is also referred to as "clonal growth" because the cells constituting a colony are those of a single strain. In addition, such cells are capable of furthermore increasing the number of cells by passage culture.

As the proliferative human hepatocytes, human small hepatocytes invented by the present inventors (JP-A 08-112092; Japanese Patent No. 3266766; U.S. Pat. No. 6,004,810, JP-A 10-179148; Japanese Patent No. 3211941, JP-A07-274951; Japanese Patent No. 3157984 and JP-A 9-313172; and Japanese Patent No. 3014322) can be used. These human small hepatocytes can, due to their excellent proliferative ability, grow rapidly in the body of a recipient to form, in a short time, a human hepatocyte population capable of demonstrating normal liver functions.

Such small hepatocytes can be collected not only by a method using centrifugation as described in the above-mentioned publications, but also with a cell sorter such as an elutriator or FACS. Alternatively, the small hepatocytes can be collected by monoclonal antibodies that specifically recognize hepatocytes that grow while forming a colony. Human hepatocytes propagated in vitro, cryopreserved hepatocytes, hepatocytes immortalized by introducing a telomerase gene or the like, and a mixture of these hepatocytes and nonparenchymal cells can also be used.

Primary Chimeric Animal

Such human hepatocytes can be transplanted into the liver through the spleen of an immunodeficient hepatopathic animal. Further, the human hepatocytes can also be transplanted directly from the portal vein. The number of human hepatocytes to be transplanted can be about 1 to 2,000,000, preferably about 500,000 to 1,000,000.

The sex of the immunodeficient hepatopathic animal is not particularly limited. Further, the age in day of the immunodeficient hepatopathic animal at the time of transplantation is not particularly limited, but the animals aged about 0 to 40 days after birth, particularly about 8 to 40 days after birth, are preferably used, because when human hepatocytes are transplanted into mice of low age in week, the human hepatocytes can grow more actively with mouse growth.

The animals after transplantation may be maintained in a usual manner. For example, the animals are maintained for about 40 to 200 days after transplantation, to obtain primary chimeric animals whose hepatocytes have been replaced partially or wholly by human hepatocytes. The chimeric animals are maintained preferably until the blood human albumin level reaches 6 mg/ml or more. When this level is reached, the liver of the chimeric animal has been replaced sufficiently by human hepatocytes, and thus human hepatocytes are contained at a high ratio in hepatocytes separated from this chimeric animal in the subsequent step. The human hepatocytes therefore can be serially transplanted in an efficient manner. For example, when the animal is a mouse, the mouse is maintained for about 40 to 120 days after transplantation of about $7.5 \times 10^5$ human hepatocytes, to attain the above-mentioned blood human albumin level (herein, a blood human albumin level reflects a replacement index of human hepatocytes).

Production of Serially Transplanted Chimeric Animal

Human hepatocytes propagated in the body of the chimeric animal can be recovered, for example, by treating the hepatic tissue of the chimeric animal with collagenase. Because the cytotoxicity of collagenase is higher to nonhuman hepatocytes than to human hepatocytes, regulation of collagenase treatment duration makes it possible that substantially only human hepatocytes are separated while the innate hepatocytes of the chimeric animal are damaged. The collagenase treatment duration varies depending on the ratio of human hepatocytes/nonhuman hepatocytes present in the liver; for example, when the blood albumin level is about 1 to 14 mg/ml, the treatment may be conducted for about 10 to 30 minutes with a solution containing about 0.01 to 0.1% by weight collagenase. In the hepatocytes thus recovered, not only human hepatocytes propagated in the body of the chimeric animal, but also a small amount of hepatic nonparenchymal cells are contained. Furthermore, the innate hepatocytes of the animal are also contained in a small amount.

The recovered hepatocytes may be used as they are for transplantation, or monoclonal antibodies which specifically recognize human hepatocytes or mouse hepatocytes may be used to increase the purity of human hepatocytes before transplantation. When the recovered hepatocytes are reacted with human hepatocyte-specific antibodies, a reacted cell population may be recovered with a flow cytometer such as a fluorescence-activated cell sorter (FACS) or a magnetic activated cell sorter (MACS). Further, when the recovered hepatocytes are reacted with mouse hepatocyte-specific antibodies, a non-reacted cell population may be recovered with FACS or MACS.

Examples of the monoclonal antibodies that specifically recognize human hepatocytes include those obtained by culturing cells of hybridoma K8216 strain produced by the present inventors (which has been deposited under FERMP-18751 since Mar. 6, 2002, with International Patent Organism Depositary (IPOD), National Institute of Advanced Industrial Science and Technology (AIST) (Tsukuba Center, Central 6, 1-1-1 Higashi, Tsukuba, Ibaraki, Japan) and deposited internationally under FERM BP-8333 since Mar. 20, 2003, with the same depositary), as well as those obtained and collected from peritoneal fluid after injection of the above hybridoma cells intraperitoneally into a mouse. Particularly, examples of the monoclonal antibodies that specifically recognize human proliferative hepatocytes include those obtained by culturing cells of hybridoma K8223 strain produced by the present inventors (which has been deposited under FERM P-18752 since Mar. 6, 2002, with International Patent Organism Depositary (IPOD), National Institute of Advanced Industrial Science and Technology (AIST) and deposited internationally under FERM BP-8334 since Mar. 20, 2003), as well as those obtained and collected from peritoneal fluid after injection of the above hybridoma cells intraperitoneally into a mouse.

In the second step, human hepatocytes that have been propagated in the body of the primary chimeric animal are transplanted into an immunodeficient hepatopathic animal of the same species as the nonhuman animal used in the first step, to produce a serially transplanted chimeric animal. The animal of the same species refers to a mouse when the animal used in the first step is a mouse or to a rat when the animal used in the first step is a rat.

The second step (serial transplantation) may be conducted once or multiple times. For example, when the second step is conducted 3 times, human hepatocytes that have been propagated in the body of the primary chimeric animal may be transplanted into a new immunodeficient hepatopathic animal to produce a serially transplanted chimeric animal, and human hepatocytes that have been propagated in the body of this serially transplanted chimeric animal may be transplanted into a new immunodeficient hepatopathic animal to produce a serially transplanted chimeric animal.

The transplantation pathway of human hepatocytes separated from the primary chimeric animal to the liver of a nonhuman animal, and the number of the hepatocytes, are the same as in the first step. Further, the age in day and sex of the nonhuman animal undergoing transplantation are also the same as in the first step.

The animals after transplantation may be maintained in a usual manner, for example for about 40 to 120 days after transplantation. Thus, serially transplanted chimeric animals whose hepatocytes have been replaced partially or wholly by human hepatocytes are obtained. By breeding the chimeric animals until the blood human albumin level reaches 0.1 mg/ml or more, preferably 1.0 mg/ml or more, the animals attain such a sufficiently high replacement index of human hepatocytes as to be usable as animal models of disease and sufficiently manifest the symptoms of human NASH. For example, when a mouse is transplanted with about $7.5 \times 10^5$ hepatocytes, the mouse will sufficiently manifest the symptoms of NASH in about 70 days, preferably about 80 days, after transplantation. Although there is no particular upper limit on a breeding period after transplantation, the animal may usually be maintained for about 400 days.

The serially transplanted chimeric animal obtained in this manner manifests the symptoms of human NASH sufficiently, but human hepatocytes that have been propagated in the body of this serially transplanted chimeric animal can further be transplanted into an immunodeficient hepatopathic animal of the same species, to obtain a serially transplanted chimeric animal. The chimeric animal thus obtained after serial transplantation for multiple times also manifests the symptoms of human NASH.

(II) Nonhuman Animal Showing the Symptoms of Human NASH

The chimeric animal thus obtained after serial transplantation conducted once or multiple times manifests the symptoms of human NASH. Specifically, at least symptoms of lipid droplet deposition, inflammatory cell infiltration and fibrosis are observed in the hepatic tissue. Human NASH-like symptoms appear much more significantly in the hepatic tissue of the serially transplanted chimeric animal than in that of the primary chimeric animal. This nonhuman animal therefore is suitable for use as a model animal of human NASH. That is, the present invention also provides a method of using, as a model animal of human NASH, the above-described nonhuman animal showing human NASH symptoms.

(III) Method for Screening a Therapeutic Agent for Human NASH

The method for screening a therapeutic agent for human NASH according to the present invention includes a step of administering a test substance to the invented nonhuman animal showing the symptoms of human NASH and a step of comparing the degree of NASH symptoms before and after administration.

The comparison of the degree of NASH symptoms before and after administration may be conducted regarding the parameters of lipid droplet deposition, inflammatory cell infiltration, and fibrosis in the hepatic tissue. When these symptoms are alleviated, the test substance can be assessed as effective in treating or ameliorating human NASH. These can be usually assessed by histological staining. Besides, comparison in apoptosis, an oxidative-stress marker, and iron deposition in the hepatic tissue is preferably conducted. By comparison in these additional parameters, more accurate screening can be achieved. When ameliorations in these parameters are observed after administration of the test substance, the test substance can be more reliably assessed as effective in treating or ameliorating NASH.

(IV) Method for Producing a Nonhuman Animal Showing the Symptoms of Fatty Liver

The method for producing a nonhuman animal showing the symptoms of fatty liver according to the present invention is a method for producing a chimeric nonhuman animal by transplanting human hepatocytes into an immunodeficient hepatopathic nonhuman animal.

Human fatty liver refers to a condition of excessive deposition of neutral fat within hepatocytes.

Immunodeficient Hepatopathic Nonhuman Animal

The immunodeficient hepatopathic nonhuman animal is as described above.

Human Hepatocytes

The human hepatocytes to be used for transplantation are as described above.

Production of Primary Chimeric Animal

Transplantation of human hepatocytes into an immunodeficient hepatopathic animal is as described above.

The animals after transplantation may be maintained in a usual manner. For example, the animals are maintained for about 40 to 200 days after transplantation, which is enough for the transplanted human hepatocytes to proliferate, to obtain primary chimeric animals showing the symptoms of fatty liver. When a mouse is transplanted with about $7.5 \times 10^5$ human hepatocytes, the mouse is maintained for about 70 to 120 days, to obtain a primary chimeric mouse showing the symptoms of fatty liver.

Further, the chimeric animal is maintained preferably until the blood human albumin level reaches 6 mg/ml or more. By breeding the chimeric animal to this extent, the animal attains a sufficiently high replacement index of human hepatocytes and can be practically used as a model animal of human fatty liver. When a mouse is transplanted with about $7.5 \times 10^5$ human hepatocytes, the mouse is maintained for about 60 to 120 days, to attain the above-mentioned blood human albumin level (a replacement index of human hepatocytes). Although there is no particularly upper limit on a breeding period after transplantation, the animal may usually be maintained for about 400 days.

(V) Nonhuman Animal Showing the Symptoms of Human Fatty Liver

The primary chimeric animal thus obtained shows the symptoms of human fatty liver. Specifically, neutral fat is deposited at least in the hepatic tissue. There is also the case where hepatocyte steatosis is recognized over about ⅓ or more of the hepatic lobules. This nonhuman animal therefore is suitable for use as a model animal of human fatty liver. That is, the present invention also provides a method of using the above-described nonhuman animal showing the symptoms of human fatty liver as a model animal of human fatty liver.

(VI) Method for Screening a Therapeutic Agent for Human Fatty Liver

The method for screening a therapeutic agent for human fatty liver according to the present invention includes a step of administering a test substance to the invented nonhuman animal showing the symptoms of human fatty liver and a step of comparing the degree of fatty liver symptoms before and after administration.

The comparison of the degree of fatty liver symptoms before and after administration may be conducted, for example, by confirming whether the degree of steatosis in a tissue section of the liver has been reduced or not. When the degree of steatosis in a tissue section of the liver has been reduced, the test substance can be assessed as effective in treating or ameliorating human fatty liver.

EXAMPLES

Hereinafter, the present invention will be described in further details with reference to Examples, but the present invention is not limited to the following examples.

Example 1

(1) Production of NASH Model Mice (1-1) Immunodeficient hepatopathic mice uPA-Tg(+/+)/SCID(+/+) mice bred in Hiroshima Prefectural Institute of Industrial Science and Technology or in PhoenixBio Co., Ltd. were used as recipient animals.

These mice were produced in the following manner. By crossing uPA-Tg mice (hemizygote, +/−) with SCIDc.b.-17 mice (homozygote, +/+), uPA-Tg(+/−)/SCID(+/−) mice having-traits of the two parents were obtained at a probability of 35.2%. Identification of uPA-Tg(+/−) mice and uPA-Tg(−/−) mice was made by a genome PCR method using uPA gene-specific sequences as primers. Further, identification of SCID (+/−) mice and SCID (−/−) mice was made by a PCR-RFLP method.

Then, the resulting uPA-Tg(+/−)/SCID(+/−) mice were backcrossed with SCID(+/+) mice to obtain uPA-Tg(+/−)/SCID (+/+) mice. As a result, uPA-Tg(+/−) mice appeared at 37.9% and SCID(+/+) mice at 52.8%. The uPA-Tg(+/−)/SCID(+/+) mice were crossed with each other to obtain uPA-Tg(+/−)/SCID(+/+) mice and objective uPA-Tg(+/+)/SCID (+/+) mice.

Here, identification of uPA gene (−/−), (+/−) and (+/+) was made in the following manner. An about 5 mm of the tail was cut off from each mouse aged 8 to 10 days after birth. To this was added 30 μl of a DNA lysis buffer (50 mM Tris (pH 8), 50 mM EDTA (pH 8), 1% SDS, 2 mg/ml Proteinase K), followed by incubation at 55° C. for 2 to 3 hours. After incubation, the sample was vigorously suspended for 15 seconds, and 170 μl of distilled water was added thereto. The sample was then incubated at 95° C. for 10 minutes to inactivate Proteinase K. The resulting reaction mixture was used as a template for PCR. One μl of the template, 2 μl of 10× Buffer (Mg$^+$), 1.6 μl of dNTP Mix (2.5 mM), 11.4 μl of distilled water, 0.4 μl of uPA-del-F primer (10 pmol/μl), 0.4 μl of uPA-del-R primer (10 pmol/μl), 0.4 μl of Tg-F primer (10 pmol/μl), 0.4 μl of uPA-high-R1 (10 pmol/μl), 2 μl of MgCl$_2$ (25 mM), 0.2 μl of Tween 20 (50%) and 0.2 μl of rTaq were mixed and subjected to PCR. The PCR profile was at 94° C. for 5 minutes, followed by 35 to 40 cycles each of at 94° C. for 30 seconds, at 62° C. for 30 seconds, and at 72° C. for 30 seconds. The sample was electrophoresed on 2% agarose gel. The uPA gene was identified as uPA (−/−) when a band was detected in the vicinity of 300 bp, uPA (+/+) when detected at 150 bp, and uPA (+/−) when detected at both 300 bp and 150 bp. The primer sequences used here were as follows:

```
uPA-del-F
5'-TTCTCTTCTCTTGCCCTCTCACA-3'    (SEQ ID NO: 1)
```

-continued

```
uPA-del-R
5'-TTGAGACCCTCAAGACAGCCA-3'      (SEQ ID NO: 2)

Tg-F
5'-ATCCCTGTGACCCCTCCC-3'         (SEQ ID NO: 3)

uPA-high-R1
5'-CTCCATACCACCCCCCTC-3'.        (SEQ ID NO: 4)
```

(1-2) Transplantation of Human Hepatocytes

The human hepatocytes used here were hepatocytes (Lot No. BD51, female child, 4-year-old) purchased from BD Gentest. These frozen hepatocytes were used after thawing according to the method described in Chise Tateno, Yasumi Yoshizane, Naomi Saito, Miho Kataoka, Rie Utoh, Chihiro Yamasaki, Asato Tachibana, Yoshinori Soeno, Kinji Asahina, Hiroshi Hino, Toshimasa Asahara, Tsuyoshi Yokoi, Toshinori Furukawa, Katsutoshi Yoshizato: Near-completely humanized liver in mice shows human-type metabolic responses to drugs. Am J Pathol 165:901-912, 2004.

Each of uPA-Tg(+/+)/SCID(+/+) mice aged 3 to 5 weeks after birth was anesthetized with ether, cut to make an about 5 mm-incision in the flank, and injected through the spleen with $7.5\times10^5$ human hepatocytes. Then, 0.02 g/ml hemostatic ε-aminocaproic acid (SIGMA) in a volume of 40 μl was administered into the peritoneal cavity of each mouse, and the spleen was returned to the peritoneal cavity, followed by closing the incision with sutures.

The reason for administration of ε-aminocaproic acid is follows: uPA produced in hepatocytes of the transgenic mouse is extracellularly secreted, resulting in an increase in blood uPA level. The uPA catalyzes proteolysis and activation of plasminogen into plasmin, and decomposes fibrin clot. ε-Aminocaproic acid that exerts a hemostatic action by inhibiting the action of plasminogen activator and plasmin was administered for preventing the mice from bleeding to death during operation.

It is known that the SCID/c.b-17 mouse used for crossing does not have T cells and B cells, but has NK cells. To prevent the transplanted human hepatocytes from being attacked by NK cells of the mouse, asialo GM1 antibody that inhibits NK activity was intraperitoneally administered on the day before transplantation and the week after transplantation.

(1-3) Separation of Human Hepatocytes from Primary Chimeric Mice

After transplantation, the mice were maintained with free access to CRF-1 containing 0.3% vitamin C (Oriental Yeast Co., Ltd.) and tap water containing 0.0125% sodium hypochlorite.

From each of the mice, blood was collected via tail vein weekly, and the human albumin level in the mouse blood was determined by turbidimetric immunoassay using a latex reagent "Eiken ALB-II" manufactured by Eiken Chemical Co., Ltd. The assay conditions were in accordance with those shown in a manual attached to the reagent.

Among the primary chimeric mice, six high-replacement mice (63 to 77 days after birth) having a blood albumin level of higher than 10 mg/ml were selected for use. From them, hepatocytes were separated by a two-step collagenase perfusion method. In the method, the concentration of collagenase was 0.05%, and the treatment time was 18 to 25 minutes. In the hepatocytes, human hepatocytes are mixed with mouse hepatocytes. The toxicity of collagenase, however, is higher to the mouse hepatocytes than to the human hepatocytes, and thus the hepatocytes containing human hepatocytes at a higher ratio can be separated.

(1-4) Production of Serially Transplanted Chimeric Mice

Each of thirty-nine uPA/SCID mice aged 3 to 5 weeks after birth was transplanted through the spleen with $7.5\times10^5$ hepatocytes separated from the primary chimeric mice. The transplantation method was the same as in the transplantation of human hepatocytes into the primary chimeric mice. The hepatocytes used here were those separated from the six primary chimeric mice. The cells separated from the six primary chimeric mice were transplanted into six, eight, ten, five, five, and five uPA-Tg(+/+)/SCID(+/+) mice, respectively.

After transplantation, the mice were maintained with free access to CRF-1 containing 0.3% vitamin C (Oriental Yeast Co., Ltd.) and tap water containing 0.0125% sodium hypochlorite.

From each of the mice, blood was collected via tail vein weekly, and the human albumin level in the mouse blood was determined by turbidimetric immunoassay using a latex reagent "Eiken ALB-II" manufactured by Eiken Chemical Co., Ltd.

After transplantation, ten serially transplanted mice died, and sixteen mice had a blood human albumin level of higher than 1 mg/ml.

(1-5) Histological Staining

Hepatic sections from the primary chimeric mice (86 days after transplantation) were subjected to hematoxylin and eosin staining and Sirius Red staining. Further, using hepatic sections from the serially transplanted chimeric mice (61 days, 89 days and 124 days after transplantation), fat deposition in hepatocytes of the chimeric mice was confirmed by Oil Red 0 staining, and fibrosis was confirmed by Sirius Red staining. Further, to specify the region of human hepatocytes in the liver of the serially transplanted chimeric mouse, immunostaining with human hepatocyte-specific cytokeratin 8/18 antibody (ICN Pharmaceuticals, Inc.) was conducted.

Oxidative stress is one cause for progress in symptoms from nonalcoholic fatty liver disease (NAFLD) to NASH. Proteins known to cause oxidative stress include CYP2E1 and 4-hydroxy-2-nonenal (4-HNE). CYP2E1 is an enzyme generating free radicals, and 4-HNE is a lipid peroxidase. Herein, hepatic sections from the primary chimeric mice and serially transplanted chimeric mice were subjected to immunostaining with human CYP2E1 antibody (AFFINITY) and human 4-HNE antibody (OXIS). The Hepatic sections from the primary chimeric mice were used as the control.

Further, because iron deposition and apoptosis are known to be observed in NASH hepatic tissue, hepatic sections from the serially transplanted chimeric mice were subjected to iron staining (MUTO PURE CHEMICALS CO., LTD.) and TUNEL staining (Serological Corporation).

(2) Test Results (2-1) Human Albumin Level in Blood

Changes in blood human albumin levels of the primary chimeric mice and serially transplanted chimeric mice are shown in FIG. 1. Out of the thirty-nine serially transplanted chimeric mice, ten mice died after transplantation. Out of the twenty-nine surviving mice, sixteen mice had a blood human albumin level of higher than 1 mg/ml. It is about 40 to 60 days after transplantation before the blood human albumin levels of these mice exceeded 1 mg/ml.

(2-2) Replacement Index of Human Hepatocytes

Figure 2:
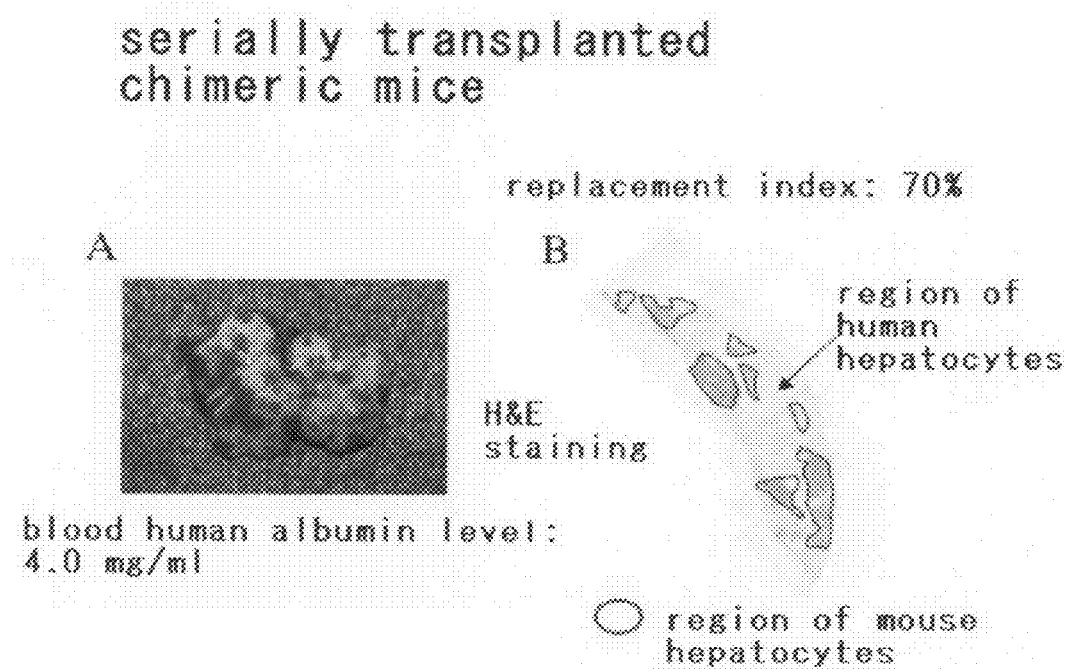
FIG. 2 Panel A is a photograph showing an external appearance of the liver of the serially transplanted chimeric mouse with a blood human albumin level of 4.0 mg/ml.
Panel B is the result of replacement index determined by HE staining of a section prepared from the right lateral hepatic lobe.

The photograph of FIG. 2A shows an external appearance of the liver of the serially transplanted chimeric mouse on day 84 after transplantation. At this time, the human albumin level in the mouse blood was 4.0 mg/ml. White portions in the liver show mainly transplanted and propagated human hepatocytes, which are observed to be more whitish due to fatty change than those in the primary chimeric mice. In the dark portions, there are mouse hepatocytes propagated due to deletion of uPA-transgenes.

FIG. 2B is a schematic diagram showing the result of hematoxylin and eosin (HE) staining of a section prepared from the right lateral lobe of the liver of the serially transplanted chimeric mouse shown in FIG. 2A. The framed regions are regions of mouse hepatocytes. The replacement index of human hepatocytes was 70%, as determined from the area ratio. The right lateral lobe accounts for about 40% of the total weight of the liver. Comparing the replacement index determined in all 7 lobes with that determined in the right lateral lobe, a high correlation is observed. It follows that the replacement index examined in the right lateral lobe virtually reflects the replacement index in the whole liver.

Reference Example

It is evident from the following experiment that comparing the replacement index determined in all 7 hepatic lobes with that determined in the right lateral hepatic lobe, a high correlation is observed in the chimeric mice. Tissue sections were prepared from all 7 lobes of the hepatic tissue in each of fourteen chimeric mice (46 to 102 days after transplantation) that had been transplanted with frozen human hepatocyte Lot. NLR (male child, 12-year-old) purchased from In Vitro Technology, and the replacement index of human hepatocytes was determined from the ratio of cytokeratin 8/18 antibody-positive area to the total section area.

Figure 10:
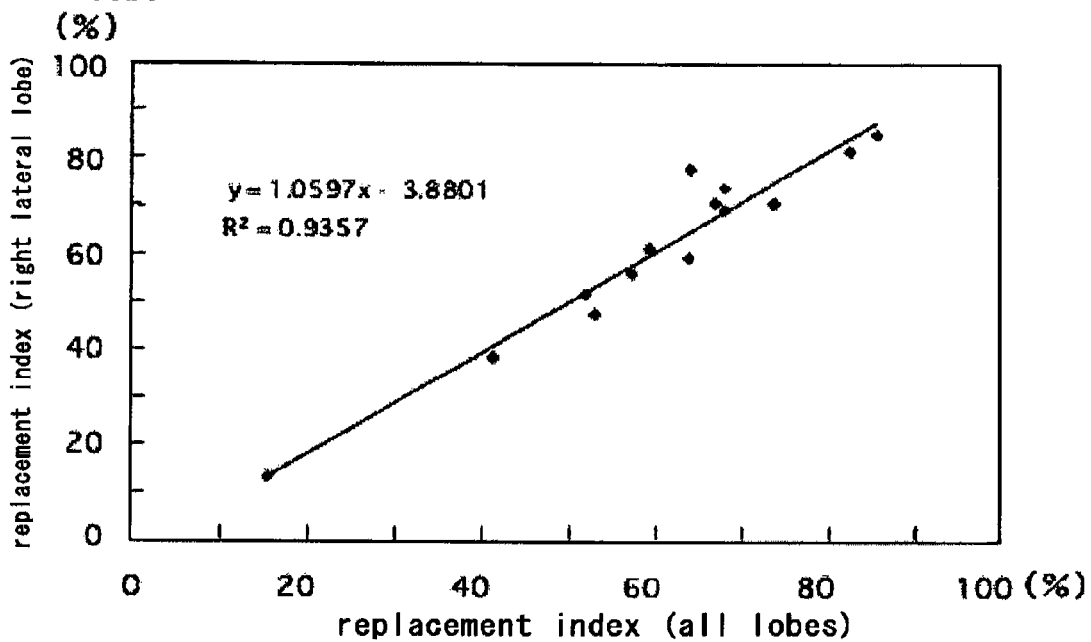
FIG. 10 is a graph showing the correlation between the replacement index in the whole liver, as determined in all 7 lobes of the hepatic tissue, and the corresponding index in the right lateral lobe.

When the correlation between the replacement index in the whole liver, as determined in all 7 lobes of the hepatic tissue, and that in the right lateral lobe was examined, the correlation coefficient $R^2=0.9357$ was obtained. FIG. 10 shows a correlation graph.

(2-3) Hepatic Tissue Image

Sections were prepared from the left medial hepatic lobe or right lateral hepatic lobe of each of the primary chimeric mice (86 days after transplantation) and the serially transplanted chimeric mice (84 days after transplantation). The sections were subjected to HE staining and Sirius Red staining.

Stained images are shown in FIG. 3. As is evident from the HE-stained image, neutrophil infiltration was observed in the serially transplanted chimeric mouse, but not in the primary chimeric mouse. Further, as is evident from Sirius Red staining, slight fibrosis was observed in the serially transplanted chimeric mouse, but not in the primary chimeric mouse.

Figure 4:
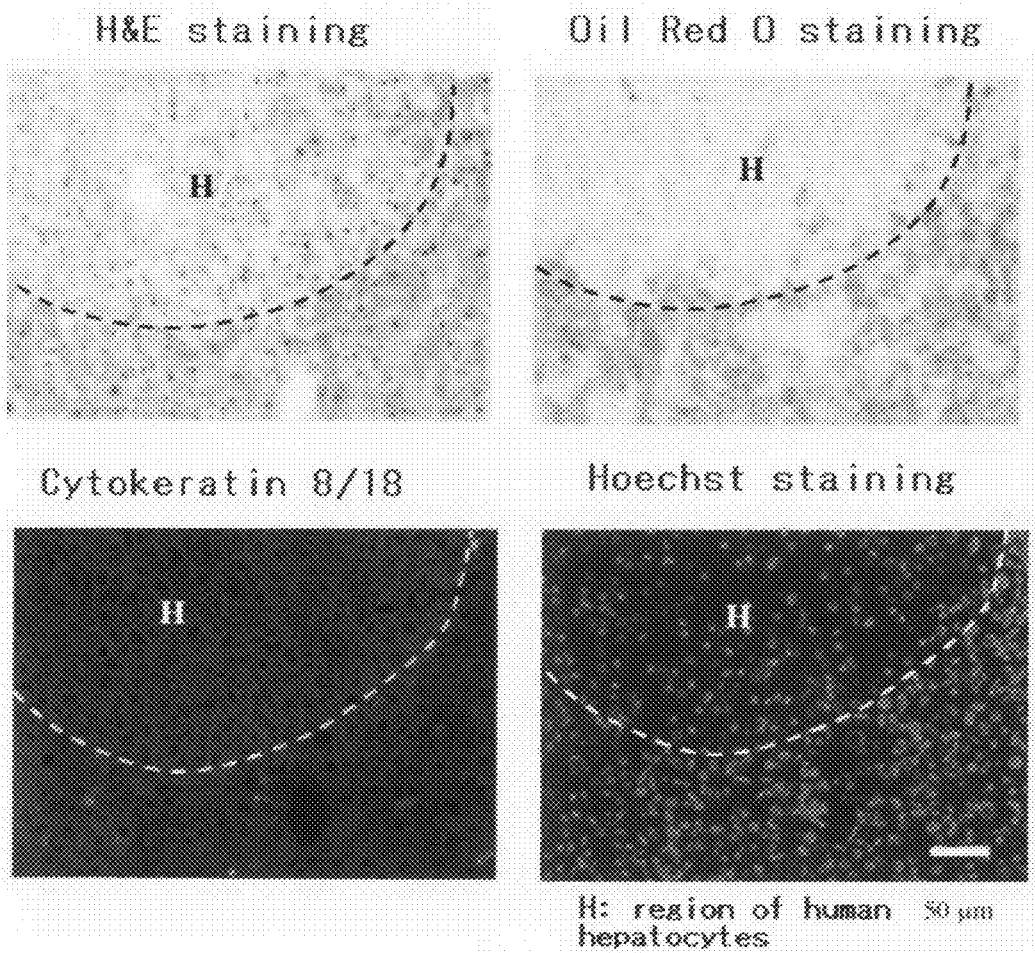
FIG. 4 shows the results of HE staining, Oil Red O staining, immunostaining for cytokeratin 8/18 and Hoechst staining of serial sections from the liver of the serially transplanted chimeric mouse (Day 61 after transplantation).

Sections were prepared from the left medial hepatic lobe or right lateral hepatic lobe of each of the serially transplanted chimeric mice (61 days, 89 days and 124 days after transplantation). The sections were subjected to HE staining and Oil Red O staining. In addition, the sections were subjected to immunostaining with human hepatocyte-specific cytokeratin 8/18 antibody, and to Hoechst staining as well. These stained images are shown in FIGS. 4, 5 and 6. In FIGS. 4 to 6, the regions stained densely by cytokeratin 8/18 immunostaining and Hoechst staining are regions of human hepatocytes.

As is evident from FIGS. 4 to 6, the serially transplanted chimeric mouse on day 61 after transplantation was found to have a normal morphology of hepatocytes as a result of HE staining and found to have a low degree of fat deposition as a result of Oil Red O staining. In the serially transplanted chimeric mice on day 89 and day 124 after transplantation, a number of swollen human hepatocytes were observed as a result of HE staining. Further, as a result of Oil Red O staining, deposition of lipid droplets was observed.

Figure 7:
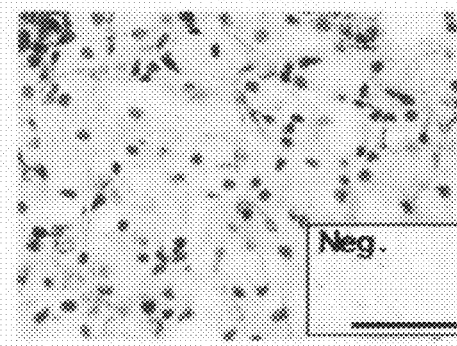
FIG. 7 shows each result of immunostaining for CYP2E1 and 4-HNE in the primary chimeric mouse liver (Day 82 after transplantation) and the serially transplanted chimeric mouse livers (Day 61 and Day 84 after transplantation).

Sections were prepared from hepatic portions replaced by human hepatocytes in the primary chimeric mouse (82 days after transplantation) and the serially transplanted chimeric mice (61 days and 84 days after transplantation). The sections were subjected to immunostaining with CYP2E1 antibody and immunostaining with 4-HNE antibody. The results are shown in FIG. 7. In each liver of the serially transplanted chimeric mice, strong expression of CYP2E1 and 4-HNE was observed. In the liver of the primary chimeric mouse, CYP2E1 was faintly stained, and 4-HNE was hardly stained.

Further, sections were prepared from hepatic portions replaced by human hepatocytes in the serially transplanted chimeric mouse (84 days after transplantation). The sections were subjected to iron staining and TUNEL staining. The results are shown in FIG. 8. Iron deposition and apoptosis were not recognized in hepatocytes in the liver of the primary chimeric mouse, while slight iron deposition and TUNEL-positive hepatocytes were observed in the liver of the serially transplanted chimeric mouse. This change was consistent with a change observed in NASH tissue.

The above description revealed that in the serially transplanted chimeric mice, neutrophil infiltration, fibrosis, deposition of lipid droplets, cellular swelling, oxidative stress, iron deposition, and apoptosis occur from 60 days after transplantation. This tissue image is very similar to an image of human hepatic tissue with NASH, and it can thus be proven that the serially transplanted chimeric mouse can be used preferably as a model animal of human NASH.

Example 2

(1) Production of Fatty Liver Model Mice (1-1) Immunodeficient hepatopathic mice The same immunodeficient hepatopathic mice as in Example 1 were used.

(1-2) Transplantation of Human Hepatocytes

As donor hepatocytes, cryopreserved cells from a 6-year-old female child (BD Gentest) or a 9-month-old male infant (In Vitro Technology) were used after thawing according to the method described in Chise Tateno, Yasumi Yoshizane, Naomi Saito, Miho Kataoka, Rie Utoh, Chihiro Yamasaki, Asato Tachibana, Yoshinori Soeno, Kinji Asahina, Hiroshi Hino, Toshimasa Asahara, Tsuyoshi Yokoi, Toshinori Furukawa, Katsutoshi Yoshizato: Near-completely humanized liver in mice shows human-type metabolic responses to drugs. Am J Pathol 165:901-912, 2004.

Each of uPA-Tg(+/+)/SCID(+/+) mice aged 3 to 5 weeks after birth was anesthetized with ether, cut to make an about 5 mm-incision in the flank, and injected through the spleen with $7.5 \times 10^5$ human hepatocytes. Then, 0.02 g/ml hemostatic ε-aminocaproic acid (SIGMA) in a volume of 40 μl was administered into the peritoneal cavity, and the spleen was returned to the peritoneal cavity, followed by closing the incision with sutures. The donor hepatocytes from the 6-year-old female child were transplanted into 41 mice, and the donor hepatocytes from the 9-month-old male infant were transplanted into 6 mice.

To prevent the transplanted human hepatocytes from being attacked by NK cells of the mouse, asialo GM1 antibody that inhibits NK activity was intraperitoneally administered on the day before transplantation and the day after transplantation.

After transplantation, the mice were maintained with free access to CRF-1 containing 0.3% vitamin C (Oriental Yeast Co., Ltd.) and tap water containing 0.0125% sodium hypochlorite.

(1-3) Histological Staining/Steatosis Grade

The chimeric mice transplanted with the hepatocytes from the 6-year-old female child were sacrificed on day 48 to day 111 after transplantation, to separate their livers. Cryosections were prepared from each liver and subjected to Oil Red O fat staining. The stained sample was photographed, and steatosis grade of each mouse liver was evaluated on a 4-stage scale (from 0 to 3), depending on the degree of Oil Red O-positive lipid droplets. A liver where fat deposition was hardly observed in hepatocytes was evaluated as Grade 0, a liver where fat deposition was observed in 33% or less of the hepatocytes was evaluated as Grade 1 (slight), a liver where fat deposition was observed in 33 to 66% of the hepatocytes was evaluated as Grade 2 (moderate), and a liver where fat deposition was observed in 66% or more of the hepatocytes was evaluated as Grade 3 (high) (Matteoni, C. A. et al.: Nonalcohlic fatty liver disease: a spectrum of clinical and pathological severity. Gastroenterology, 116:1413-1419, 1999).

(2) Test Results

The results are shown in FIG. 9. FIG. 9B is a graph showing the relationship between the number of elapsed days after transplantation and steatosis grade, and FIG. 9A shows Oil Red O-stained images of the respective cryosections evaluated as Grades 0, 1, 2 and 3.

Up to 60 days after transplantation, steatosis grade was as low as 0 or 1 and lipid droplets were a few. From 70 days after transplantation, steatosis grade was increased, and large lipid droplets were observed. Even some showed fat deposition throughout the hepatocyte regions. In the liver of the chimeric mouse, fatty change was hardly observed until 60 days or so after transplantation, but from 70 days after translation, the number of mice showing fatty change was increased. It was considered that the degree of fatty change increases with the number of elapsed days after transplantation.

Images of the hepatic tissues from 70 days after transplantation were very similar to a tissue image of human fatty liver. From this result, the primary chimeric mouse transplanted with human hepatocytes can be preferably used as a model animal of human fatty liver.

INDUSTRIAL APPLICABILITY

The nonhuman animal of the present invention can be preferably used as a model animal of human nonalcoholic steatohepatitis or a model animal of human fatty liver for screening a therapeutic agent for such diseases.

The invention claimed is:

1. A rodent showing a symptom of human nonalcoholic steatohepatitis consisting of lipid droplet deposition, inflammatory cell infiltration and fibrosis in the hepatic tissue, the rodent being obtained by a method comprising:
   a first step of transplanting human hepatocytes into an immunodeficient hepatopathic rodent to produce a chimeric rodent; and
   a second step of transplanting human hepatocytes that are propagated in the body of the chimeric rodent into an immunodeficient hepatopathic rodent of the same species as the immunodeficient hepatopathic rodent described above, the second step being conducted once or a plurality of times,
   wherein the resultant immunodeficient hepatopathic rodent has a blood human albumin level of 0.1 mg/ml or more and shows a symptom of human nonalcoholic steatohepatitis consisting of lipid droplet deposition, inflammatory cell infiltration and fibrosis in the hepatic tissue.

2. The rodent according to claim 1, which is obtained by the method in which the second step is conducted once.

3. A model rodent of human nonalcoholic steatohepatitis, which is obtained by a method comprising:
   a first step of transplanting human hepatocytes into an immunodeficient hepatopathic rodent to produce a chimeric rodent; and
   a second step of transplanting human hepatocytes that are propagated in the body of the chimeric rodent into an immunodeficient hepatopathic rodent of the same species as the immunodeficient hepatopathic rodent described above, the second step being conducted once or a plurality of times,
   wherein the resultant immunodeficient hepatopathic rodent has a blood human albumin level of 0.1 mg/ml or more and shows a symptom of human nonalcoholic steatohepatitis consisting of lipid droplet deposition, inflammatory cell infiltration and fibrosis in the hepatic tissue.

4. The model rodent according to claim 3, which is obtained by the method in which the second step is conducted once.

5. A method for screening a therapeutic agent for human nonalcoholic steatohepatitis, which comprises
   a step of administering a test substance to a rodent;
   a step of comparing the degree of symptoms of lipid droplet deposition, inflammatory cell infiltration and fibrosis in the hepatic tissue before and after administration; and
   a step of assessing a test substance alleviating these symptoms as a therapeutic agent for human nonalcoholic hepatitis,
   the rodent being obtained by a method comprising:
   a first step of transplanting human hepatocytes into an immunodeficient hepatopathic rodent to produce a chimeric rodent; and
   a second step of transplanting human hepatocytes that are propagated in the body of the chimeric rodent into an immunodeficient hepatopathic rodent of the same species as the immunodeficient hepatopathic rodent described above, the second step being conducted once or a plurality of times,
   wherein the resultant immunodeficient hepatopathic rodent has a blood human albumin level of 0.1 mg/ml or more and shows a symptom of human nonalcoholic steatohepatitis.

6. The method according to claim 5, wherein the rodent is obtained by the method in which the second step is conducted once.

7. A method for producing a rodent showing a symptom of human nonalcoholic steatohepatitis consisting of lipid droplet deposition, inflammatory cell infiltration and fibrosis in the hepatic tissue, which comprises
   a first step of transplanting human hepatocytes into an immunodeficient hepatopathic rodent to produce a chimeric rodent; and
   a second step of transplanting human hepatocytes that are propagated in the body of the chimeric rodent into an immunodeficient hepatopathic rodent of the same species as the immunodeficient hepatopathic rodent described above, the second step being conducted once or a plurality of times,
   wherein the resultant immunodeficient hepatopathic rodent has a blood human albumin level of 0.1 mg/ml or more and shows a symptom of human nonalcoholic steatohepatitis consisting of lipid droplet deposition, inflammatory cell infiltration and fibrosis in the hepatic tissue.

8. The method according to claim 7, wherein the second step is conducted once.

9. A method for screening a therapeutic agent for human fatty liver, which comprises
   a step of administering a test substance to a chimeric rodent obtained by transplanting human hepatocytes into an immunodeficient hepatopathic rodent;
   a step of comparing the degree of steatosis in the hepatic tissue before and after administration; and
   a step of assessing a test substance reducing the degree of steatosis in the hepatic tissue as a therapeutic agent for human fatty liver.

10. The rodent according to claim 1, wherein the immunodeficient hepatopathic rodent is an immunodeficient uPA transgenic rodent.

11. The model rodent according to claim 3, wherein the immunodeficient hepatopathic rodent is an immunodeficient uPA transgenic rodent.

12. The method according to claim 5, wherein the immunodeficient hepatopathic rodent is an immunodeficient uPA transgenic rodent.

13. The method according to claim 7, wherein the immunodeficient hepatopathic rodent is an immunodeficient uPA transgenic rodent.

14. The method according to claim 9, wherein the immunodeficient hepatopathic rodent is an immunodeficient uPA transgenic rodent.

* * * * *

```
SEQUENCE LISTING

<160> NUMBER OF SEQ ID NOS: 4

<210> SEQ ID NO 1
<211> LENGTH: 23
<212> TYPE: DNA
<213> ORGANISM: Artificial sequence
<220> FEATURE:
<223> OTHER INFORMATION: Oligonucleotide used as a primer

<400> SEQUENCE: 1
ttctcttctc ttgccctctc aca                                            23

<210> SEQ ID NO 2
<211> LENGTH: 21
<212> TYPE: DNA
<213> ORGANISM: Artificial sequence
<220> FEATURE:
<223> OTHER INFORMATION: Oligonucleotide used as a primer

<400> SEQUENCE: 2
ttgagaccct caagacagcc a                                              21

<210> SEQ ID NO 3
<211> LENGTH: 18
<212> TYPE: DNA
<213> ORGANISM: Artificial sequence
<220> FEATURE:
<223> OTHER INFORMATION: Oligonucleotide used as a primer

<400> SEQUENCE: 3
atccctgtga cccctccc                                                  18

<210> SEQ ID NO 4
<211> LENGTH: 18
<212> TYPE: DNA
<213> ORGANISM: Artificial sequence
<220> FEATURE:
<223> OTHER INFORMATION: Oligonucleotide used as a primer
```

```
<400> SEQUENCE: 4
ctccatacca ccccctc                                                    18
```